United States Patent [19]

Fitton et al.

[11] 4,124,619
[45] Nov. 7, 1978

[54] PREPARATION OF ESTERS OF HYDROXY TIGLIC ALDEHYDE

[75] Inventors: Peter Fitton, Pequannock; Harold Moffet, Fairlawn, both of N.J.

[73] Assignee: Hoffmann-La Roche Inc., Nutley, N.J.

[21] Appl. No.: 780,553

[22] Filed: Mar. 23, 1977

Related U.S. Application Data

[63] Continuation of Ser. No. 581,458, May 28, 1975, abandoned.

[51] Int. Cl.$^2$ ............................................. C07C 67/28
[52] U.S. Cl. .................................... 260/410.6; 560/8; 560/20; 560/21; 560/22; 560/56; 560/64; 560/100; 560/112; 560/238; 560/262; 560/264

[58] Field of Search .................. 260/491, 469, 476 R, 260/473 R, 405, 410.6; 560/56, 112, 264, 100, 8, 20–22, 64

[56] References Cited

U.S. PATENT DOCUMENTS

| 3,732,287 | 5/1973 | Himmele et al. ..................... 260/491 |
| 3,880,913 | 4/1975 | Smith ................................... 260/491 |

*Primary Examiner*—Vivian Garner
*Attorney, Agent, or Firm*—Samuel L. Welt; Bernard S. Leon; George W. Johnston

[57] ABSTRACT

Preparation of carboxylic acid esters of γ-hydroxy-tiglic-aldehyde from bismonocarboxylic acid esters of but-2-en-1,4-diol via 1,4-diacetoxy-2-formyl butane including intermediates in this synthesis.

1 Claim, No Drawings

PREPARATION OF ESTERS OF HYDROXY TIGLIC ALDEHYDE

This is a continuation of application Ser. No. 581,458 filed May 28, 1975, entitled "PREPARATION OF ESTERS OF HYDROXY TIGLIC ALDEHYDE" now abandoned.

BACKGROUND OF THE INVENTION

The carboxylic acid esters of γ-hydroxy-tiglic aldehyde are known intermediates for vitamin A and various perfumistic products. These esters have been prepared from 1,1-dimethoxy-2-methyl-but-3-en-2-ol. See U.S. Pat. No. 3,760,004, Sept. 18, 1973, Freyschlag et al. and U.S. Pat. No. 3,347,930, Oct. 17, 1967, Freyschlag et al. Another starting material such as the bismonocarboxylic acid ester of but-1-ene-3,4-diol also has been used as a starting material for these esters of γ hydroxy-tiglic-aldehyde. See U.S. Pat. No. 3,732,287—Himmele et al., May 8, 1973.

Recently in U.S. Pat. No. 3,661,980, Himmele et al., May 9, 1972, it has been proposed to prepare these esters of γ-hydroxy-tiglic aldehyde from esters of but-2-ene-1,4-diol. However, this synthesis as well as the synthesis from the esters of but-1-ene-3,4-diol has not proven to be economical since pressures of from 300 to 1,000 atmospheres are utilized to obtain the desired product. The use of these very high pressures involves the use of expensive equipment and costly handling procedures which mitigates against the commercialization of this process. Therefore, a simple and economic process for converting these relatively inexpensive but-2-ene diols to esters of γ-hydroxy tiglic aldehyde is desired.

SUMMARY OF THE INVENTION

In accordance with this invention, biscarboxylic acid esters of but-2-ene-1,4-diols which have the formula:

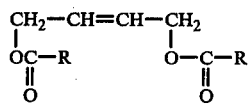
I wherein R is alkyl or aryl;
can be converted to the carboxylic acid ester of γ-hydroxy-tiglic aldehyde which has the formula:

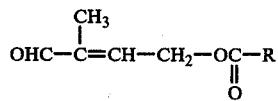
II wherein R is as above;
via the following intermediates:

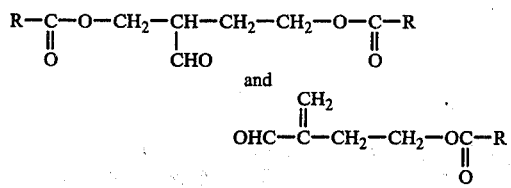
III
and
IV wherein R is as above;
utilizing pressures of from 30 to 150 atmospheres. Therefore, the process of this invention allows one to convert the compound of formula I to the compound of formula II in high yields without utilizing expensive high pressure equipment and handling techniques.

As used throughout this specification, the term "alkyl" comprehends straight chain and branched chain, saturated aliphatic hydrocarbon groups containing from 1 to 18 carbon atoms. The term "alkyl" included lower alkyl groups containing from 1 to 7 carbon atoms such as methyl, ethyl, propyl, isopropyl, etc. as well as higher alkyl groups containing from 8 to 18 carbon atoms such as dodecyl, tetradecyl, octyl, etc.

As used therein, the term "aryl" signifies mononuclear aromatic hydrocarbon groups such as phenyl, which can be substituted in one or more positions with a halogen, a nitro, lower alkyl or lower alkoxy substituent as well as polynuclear aryl groups such as naphthyl, anthryl, etc. which can be unsubstituted or substituted with one or more of the aforementioned groups. The preferred aryl groups are the substituted and unsubstituted mononuclear aryl groups, particularly phenyl.

As used herein, the term "halogen" or "halo", unless otherwise stated, comprehends all four halogens, i.e., fluorine, chlorine, bromine and iodine. The term "lower alkoxy" as used herein comprehends lower alkoxy groups having from 1 to 7 carbon atoms such as methoxy, ethoxy, n-butoxy, as well as isopropoxy.

Among the preferred but-2-ene-1,4-diol esters of formula I which can be utilized as starting materials are included the following:
but-2-ene-1,4-diol diformate;
but-2-ene-1,4-diol diacetate;
but-2-ene-1,4-diol dipropionate;
but-2-ene-1,4-diol dibutyrate;
but-2-ene-1,4-diol diisobutyrate;
but-2-ene-1,4-diol dipalmitate;
but-2-ene-1,4-diol dibenzoate; and
but-2-ene-1,4-diol p-chlorobenzoate.

The compound of formula I is converted to the compound of formula III by treating the compound of formula I with a mixture of carbon monoxide and hydrogen in the presence of a rhodium catalyst. In carrying out this reaction, temperatures of 50° C. to 100° C. are utilized. Furthermore, the reaction is carried out at pressures of from 30–150 atmospheres. In carrying out this reaction, the carbon monoxide and hydrogen are used in a ratio of from 1:2 to 2:1 parts by volume.

Furthermore, this reaction is generally carried out in an inert organic solvent. Any conventional inert organic solvent can be utilized in carrying out this reaction. Among the preferred solvents are the hydrocarbon solvents such as benzene, xylene, toluene, cyclohexane, or octane; ethers such as diethyl ether, tetrahydrofuran or dioxane; esters such as ethyl acetate or methyl propionate; or alcohols such as methanol or n-butanol.

In carrying out this reaction, a rhodium catalyst is utilized. Generally, it is preferred to carry out this reaction in the presence of a carbonyl complex of rhodium which forms by the addition of carbon monoxide and hydrogen to the reaction medium. The rhodium catalyst is present in catalytic amounts. Generally, it is preferred to use 0.0001 to 2% by weight of rhodium calculated as metal based upon the weight of the compound of formula I, with amounts of from about 0.01 to 0.1% by weight being particularly preferred. Where a carbonyl complex of rhodium is utilized, this complex will form under the conditions of the reaction. Also, it is possible to prepare the carbonyl complex separately prior to supplying the starting material of formula I to the reaction medium.

In accordance with a particularly preferred embodiment of this invention the catalyst used is rhodium carbonyl complex modified with a phosphorous compound of the formula:

wherein $R_1$ is $-OR_4$ or $R_4$; $R_2$ is $-OR_5$ or $-R_5$; $R_3$ is $-OR_6$ or $-R_6$; and $R_4$, $R_5$ and $R_6$ are lower alkyl or aryl.

In accordance with this invention, it is preferred to use the modifying agent in an amount of from 1 to 4 moles of the phosphorous compound per mole of rhodium or of the rhodium complex.

The formation of the compound of formula III is carried out by placing the compound of formula I in an inert organic solvent with the desired amount of catalyst in a pressure vessel and reacting it in this pressure vessel with a mixture of carbon monoxide and hydrogen at pressures of from 20 to 100 atmospheres pressure and at temperatures of from 50°–100° C.

The compound of formula III is converted to the compound of formula IV by pyrolysis. Any conventional method of pyrolysis can be utilized to convert the compound of formula III to the compound of formula IV. Among the preferred methods of pyrolysis is to heat the compound of formula III with an acid catalyst to a temperature of from 70° C. to 250° C. This reaction can be carried out at atmospheric pressure. On the other hand, this reaction can be carried out under vacuum such as from 1 mm Hg to 700 mm Hg. The pyrolysis may be carried out without the presence of any solvent. Any conventional acid catalyst can be utilized in carrying out this pyrolysis. Among the preferred acid catalysts are the strong organic acids as well as the inorganic acids. Among the preferred inoganic acids are the hydrohalic acids such as hydrochloric acid, hydrobromic acid, etc. as well as sulfuric acid. Among the preferred strong organic acids are p-toluenesulfonic acid, trifluoroacetic acid and trichloroacetic acid. Where the reaction is carried out at temperatures of from 120°–150° C., no acid catalyst need be present. However, it is generally preferred to utilize an acid catalyst since the utilization of this catalyst allows the pyrolysis to take place at lower temperatures. Therefore, if temperatures of from 70°–150° C. are utilized in the pyrolysis reaction, it is best to carry out the pyrolysis in the presence of an acid catalyst.

The compound of formula IV can be converted to the compound of formula II by treating the compound of formula IV with hydrogen utilizing a conventional hydrogenation catalyst such as palladium or platinum. Generally, it is preferred to use a sulfur poisoned palladium or platinum catalyst in carrying out this reaction. In carrying out this reaction, temperature and pressure are not critical and this reaction can be carried out at room temperature. Generally, it is preferred to utilize a temperature of from 0° C. to 180° C. In general, this reaction is carried out in the presence of an inert organic solvent. Any conventional inert organic solvent can be utilized to carry out this reaction. Among the preferred solvents are the solvents mentioned hereinbefore with the aromatic hydrocarbon solvents such as benzene, xylene and toluene being especially preferred.

The following Examples are illustrative but not limitative of the invention. In the Examples, all temperatures are in degrees centigrade.

EXAMPLE 1

Hydridocarbonyltris(triphenylphosphine) rhodium (I)

To a refluxing solution of triphenylphosphine (52.4 g.) in ethanol (400 ml.) was added in rapid succession a solution of rhodium trichloride (40% by weight rhodium metal, 4.6 g.) in ethanol (1600 ml.), formalin (200 ml.) and a solution of sodium borohydride (4 g.) in ethanol (400 ml.). After refluxing for 15 minutes a solution of sodium borohydride (4 g.) in ethanol (400 ml.) was added and the mixture was refluxed for a further 15 minutes. After cooling, the mixture was filtered and the precipitate was washed with water (3 × 200 ml.), ethanol (2 × 200 ml.) and petroleum ether (b.p. = 40° to 60° C.) (3 × 200 ml.). The precipitate was then air-dried to give hydridocarbonyltris(triphenylphosphine) rhodium (I) (15.2 g.) (crude).

Crude hydridocarbonyltris(triphenylphosphine)rhodium (I) (10 g.) from the reaction above was added to a refluxing solution of triphenylphosphine (20 g.) in ethanol (800 ml.). To this mixture was added a solution of sodium borohydride (8 g.) in ethanol (800 ml.). After refluxing for 30 minutes, the mixture was cooled and filtered. The precipitate was washed with water (2 × 200 ml.) ethanol (3 × 200 ml.) and petroleum ether (b.p. = 40° to 60° C.) (3 × 200 ml.) and air dried to give pure hydridocarbonyltris(triphenylphosphine) rhodium (I) (9.51 g.).

EXAMPLE 2

A solution of 1,4-diacetoxy-2-butene (170 g.) and hydridocarbonyltris(triphenylphosphine)rhodium (I) (0.5 g.) in benzene (170 g.) was heated to 75° C. in a 1 liter stainless steel bomb under a pressure of 2000 p.s.i.g. of synthesis gas (50% by volume $H_2$, 50% by volume CO). After 90 minutes when the gas uptake had ceased, the bomb was cooled rapidly and vented. Removal of benzene by distillation from the resulting solution left an oil (198.5 g.). Rapid distillation of this crude product gave 1,4-diacetoxy-2-formylbutane (153.7 g.) 77% yield, b.p. 112°–115° C./0.75 mm Hg.

EXAMPLE 3

A solution of 1,4-diacetoxy-2-butene (170 g.) and hydridocarbonyltris(triphenylphosphine) rhodium (I) (0.5 g.) in benzene (340 g.) was heated in a bomb at 75° C. under 2000 psig of a synthesis gas (50% by volume $H_2$ and 50% by volume CO gas). After a few hours, the bomb was cooled and vented and the benzene was removed from the reaction product by distillation. The resulting crude 1,4-diacetoxy-2-formylbutane was then heated to 120°–130° C. in a distillation apparatus under a vacuum of 5 mm Hg. and a distillate (190.3 g. b.p. 60°–80° C.) was collected. The distillate on redistillation gave acetic acid, 2-formyl-4-acetoxybutene (127.1 g., 90.3% yield, b.p. 77°–79° C./6 mm Hg) and 1,4-diacetoxy-2-formyl butane (12.5 g., 6.2% yield, b.p. 110°–113° C./1 mm Hg.

EXAMPLE 4

The reaction as described in Example 3 was repeated. After removal of the benzene, p-toluenesulphonic acid (1 g.) was added to the crude 1,4-diacetoxy-2-formylbutane and this solution was heated to 100°–110° C. in a distillation apparatus under a vacuum of 5 mmHg. The collected distillate was combined with the distillates from two other identical reactions and redistilled to give 2-formyl-4-acetoxybutene (395.7 g., 94% yield, b.p. 72°–75° C./5 mm Hg.).

EXAMPLE 5

1,4-diacetoxy-2-formylbutane (105 g.) was heated to 180°–210° C. in a distillation apparatus under a vacuum of 350 mm Hg. A distillate was collected, which on redistillation gave 2-formyl-4-acetoxybutene (65.5 g., 89% yield, b.p. 68°–72° C./5 mm Hg.).

EXAMPLE 6

A solution of 1,4-diacetoxy-2-butene (85 g.) and hydridocarbonyltris(triphenylphosphine) rhodium (I) (0.25 g.) in benzene (170 g.) was heated to 80° C. in a stainless steel bomb. The bomb was pressured to 850 psig with carbon monoxide and then to 1700 psig with hydrogen. After 4 hours, the reaction was complete. After cooling and venting the bomb, the solution was removed and the benzene was removed to give 1,4-diacetoxy-2-formylbutane (96 g., 110°–112° C./1 mm Hg.).

EXAMPLE 7

A mixture of 1,4-diacetoxy-2-butene (170 g.), triphenylphosphite (0.51 g.), 5% rhodium on charcoal (1.12 g.) and benzene (340 g.) was loaded into a 1 liter stainless steel autoclave and heated with stirring to 85° C. The autoclave was then pressured to 2000 psig with synthesis gas. When gas uptake had ceased (approximately 3 hours), the autoclave was cooled to room temperature and vented. The reaction mixture was filtered and heated under vacuum until all the benzene had been removed. After the addition of p-toluenesulphonic acid (0.5 g.), the reaction product was heated in an oil bath at 105°–110° C. under a vacuum of 5 mm Hg. and the distillate so produced was collected and then fractionally distilled to give 2-formyl-4-acetoxybutene (126.3 g., 90% yield, b.p. 67°–72° C./6 mm Hg.).

EXAMPLE 8

The procedure of Example 7 was repeated using 1,4-diacetoxy-2-butene (170 g.) and 5% by weight rhodium on 95% by weight charcoal (1.12 g.) in benzene (340 g.). The reaction took 6 hours to go to completion. Work-up in the manner of Example 7 gave a 54% yield of 2-formyl-4-acetoxybutene.

EXAMPLE 9

A solution of 1,4-diacetoxy-2-butene (170 g.), (1,5-cyclooctadiene) rhodium (acetylacetonate) (0.17 g.) and triphenylphosphite (0.51 g.) was heated to 75° C. in a 1 liter stainless steel autoclave under a pressure of 2,000 psig of synthesis gas. After a few hours, the reaction was complete. After cooling and venting, the resulting solution was distilled to remove benzene. P-toluenesulphonic acid (0.5 g.) was added and the mixture was distilled (115°–120° C./5 mmHg). The resulting distillate was fractionated to give 2-formyl-4-acetoxybutene (118.1 g., 89% yield).

EXAMPLE 10

A solution of N,N,N′,N′-tetramethylthiourea (4.58 g.) in acetone (1500 ml.) was added to 5% palladium on charcoal (100 g.). After stirring for 10 minutes at room temperature, the acetone was removed by heating on a rotovapor (80° C./300 mm Hg.) to leave a free flowing solid which was dried by heating overnight in a vacuum oven (100° C./300 mm Hg.). This material (105.2 g.) was used as a catalyst for the isomerization of 2-formyl-4-acetoxybutene to γ-acetoxytiglic aldehyde.

EXAMPLE 11

The 5% by weight palladium —4.58% tetramethylthiourea on charcoal catalyst (9 g.) (prepared as in Example 10) was added to a solution of 2-formyl-4-acetoxybutene (450 g.) in xylene (1.5 l.). The mixture was heated with stirring to 100° C. under nitrogen. A stream of 6% hydrogen in argon (960 ml/min) was passed through the mixture. After 570 minutes, glc analysis showed that 61% of the 2-formyl-4-acetoxybutene charged had been converted to products. Of these products, 80% was γ acetoxytiglic aldehyde and 20% was 2-formyl-4-acetoxybutane.

We claim:

1. A process for preparing a formyl compound of the formula:

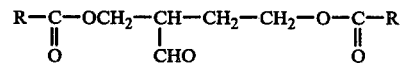

wherein R is alkyl or mononuclear aryl; wherein said aryl may be unsubstituted or substituted in one or more positions with halogen, nitro, lower alkyl or lower alkoxy;

comprising reacting in an inert organic solvent medium a compound of the formula:

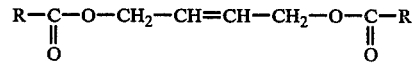

wherein R is as above;
with hydrogen and carbon monoxide in the presence of hydridocarbonyltris(triphenylphosphine)rhodium (I) at a temperature of from 50° C. to 100° C. and a pressure of from 30 atmospheres to 150 atmospheres.

* * * * *